United States Patent

Schreiner et al.

[11] Patent Number: 6,019,001
[45] Date of Patent: Feb. 1, 2000

[54] PROCESS AND DEVICE FOR THE ULTRASONIC EXAMINATION OF DISK ELEMENTS OF UNKNOWN CONTOURS SHRUNK ONTO SHAFTS

[75] Inventors: Thomas Schreiner, Mülheim an der Ruhr; Hans-Peter Lohmann, Wesel-Obrighoven, both of Germany

[73] Assignee: Siemens Aktiengesellschaft, Munich, Germany

[21] Appl. No.: 09/043,836

[22] PCT Filed: Sep. 13, 1996

[86] PCT No.: PCT/DE96/01733

§ 371 Date: Jun. 30, 1998

§ 102(e) Date: Jun. 30, 1998

[87] PCT Pub. No.: WO97/13144

PCT Pub. Date: Apr. 10, 1997

[30] Foreign Application Priority Data

Sep. 29, 1995 [DE] Germany ............................ 195 36 447

[51] Int. Cl.[7] .................................................. G01N 29/04
[52] U.S. Cl. .................................. 73/640; 73/618; 73/621
[58] Field of Search .............................. 73/640, 641, 619, 73/620, 621, 628, 633, 602, 618, 649

[56] References Cited

U.S. PATENT DOCUMENTS

| 4,577,507 | 3/1986 | Jestrich et al. | 73/621 |
| 4,774,842 | 10/1988 | Kollar et al. | 73/640 |
| 5,408,884 | 4/1995 | Sabourin | 73/649 |
| 5,567,881 | 10/1996 | Myers | 73/640 |
| 5,576,492 | 11/1996 | Phalin | 73/640 |

FOREIGN PATENT DOCUMENTS

| 0 126 383 B1 | 5/1984 | European Pat. Off. . |
| 37 15914 A1 | 5/1987 | Germany . |
| 63-309852 | 6/1987 | Japan . |
| 2 266 367 | 10/1992 | United Kingdom . |
| 2 285 129 | 6/1995 | United Kingdom . |

*Primary Examiner*—Hezron Williams
*Assistant Examiner*—Helen C. Kwok
*Attorney, Agent, or Firm*—Herbert L. Lerner; Laurence A. Greenberg

[57] ABSTRACT

Method and apparatus for ultrasound testing of disc bodies which are shrunk onto shafts and have an unknown contour.

The invention relates to a method and an apparatus for ultrasound testing of a disc body (2), which is shrunk onto a shaft (1), in the region of the shrink seating (3) and of the adjacent shrinkage influence zone, the disc body (2) having side pieces (4, 5) which taper radially outwards from the shrink seating in cross-section. The contour of the disc body (2) is scanned and its geometry is derived in this way. A geometric reflection surface is determined. Test parameters and test positions are determined from the disc body geometry in accordance with a predetermined test technique, and ultrasound test heads (9, 10) are coupled, using the determined test parameters, to the side pieces (4, 5) in order to cover the determined test paths. The associated apparatus has a geometry identification device which detects the geometry of the disc body (2) before the actual test procedure. The invention makes it possible to test turbine discs in a time-saving manner, without it being necessary to known their geometry before the test.

17 Claims, 2 Drawing Sheets

PROCESS AND DEVICE FOR THE ULTRASONIC EXAMINATION OF DISK ELEMENTS OF UNKNOWN CONTOURS SHRUNK ONTO SHAFTS

BACKGROUND OF THE INVENTION

The invention relates to a method and an apparatus for ultrasound testing of a disc body which is shrunk onto a shaft, in particular a disc of a low-pressure turbine rotor.

Stress-corrosion cracks can lead to progressive damage when rotating parts are subject to dynamic loading, such as a disc on a rotor of a low-pressure turbine, for example. It is thus necessary to examine such components at predetermined intervals for stress corrosion cracks. Discs which are arranged on a rotor such that they are locked by axial or radial pins against rotation cannot be tested by dismantling the rotor, for economic reasons. It is thus recommended that an ultrasound test has to be carried out in the region of the shrink seating and of the adjacent material regions, in particular in the region of the hub inner surface and the axial anti-rotation locks. However, the geometry of the disc is extremely complicated for ultrasound testing using ultrasound test heads in the inaccessible hub inner region and in the vicinity of the anti-rotation locks. Furthermore, additional problems are associated with carrying out the ultrasound tests in a reproducible manner. Only the side pieces of the disc are available as a coupling surface for the ultrasound test heads. Accessibility to the coupling surfaces on the disc is frequently restricted by adjacent discs. A further problem is that the sound paths to reflectors governed by the geometry (for example an anti-rotation lock) and to any cracks which may be present originating from the hub bore may be identical.

In order to overcome these difficulties, EP 0 126 383 B1 has proposed a method for ultrasound testing of disc bodies, which are shrunk onto shafts, in the region of the shrink seating, and a device for carrying out the method. According to this proposal, special angled test heads are arranged together with measuring probes on a metal template sheet, which is matched to the respective side piece section, with the aid of a test head holder. Such special angled test heads are then moved to, and coupled to, the contour of the section of the relevant side piece by means of a manipulator arm. A specific subregion of the disc is assigned a metal template sheet. The correct axial and radial positioning of the metal template sheet is indicated by test probes. In other words, the measuring probes, which are designed in particular as inductive measuring probes, are arranged on each metal template sheet in order to monitor the positioning of the angled test heads, and the test heads themselves are in each case arranged at quite specific positions, and with quite specific relationships to one another, in order to ensure the conversion of the ensonification and squint angles of the relevant test heads to the ensonification directions required for the specific test region, when coupling to a specific position on a disc side piece. This results in a multiplicity of metal template sheets being necessary for testing a disc. The manufacture of such metal template sheets is dependent on the geometry of the side pieces being known. The preparatory work which is required to carry out the ultrasound test is relatively complex, since ultrasound testing is not possible until after comprehensive, time-consuming analysis of the drawings and after design and production of manipulation aids in the form of templates.

The brief extract from Japanese Patent Application JP-A 63-309 852, from Patents Abstracts of Japan P-854 Apr. 11, 1989, Vol. 13/No. 146 describes a method for crack identification in a body having an essentially unknown contour which is curved in a continuous convex manner. The contour is determined using a scanning device which can be moved in three mutually independent directions, is stored in a memory, and these stored data are used to control the drive mechanism of a manipulator. A distance sensor is mounted on the scanning device. The data stored in the memory are used in a computer to calculate the position of a test probe, so that the latter is guided essentially at right angles to the surface of the body, at a predetermined distance from it. A further method for determining the contour of a body and for identification of cracks in the body is described in GB 2 266 367 A. This method is carried out for determining an inner and an outer contour of a three-dimensional test object as well as for finding deeply located defects in metallic components, for example turbine blades, pipelines or valves. The contour of the test object is determined using an ultrasound test head coupled to it, in such a manner that the respective position of the ultrasound test head is detected via LED probes.

SUMMARY OF THE INVENTION

The present invention is based on the object of specifying a method and an apparatus using which an ultrasound test can be carried out even without any prior knowledge of the disc body geometry.

According to one aspect of the invention, there is provided a method for ultrasound testing of a disc body which is shrunk onto a shaft, in the region of a shrink seating and of an adjacent shrinkage influence zone, the disc body having side pieces which taper radially outward from the region of a shrink seating in cross-section, the method comprising: scanning the contour of the disc body; determining a geometric reflection surface for which occurrences of defects must be taken into account; deriving a disc body geometry from the results of said scanning the contour and said determining a geometric reflection surface; determining test parameters and test positions according to a predetermined test technique for ultrasound test heads, taking into account the disc body geometry; and coupling ultrasound test heads, using the determined test parameters, to the side pieces in order to cover test paths. According to a further aspect of the invention, there is provided an apparatus for ultrasound testing of a disc body, which is shrunk onto a shaft installed in a turbine system, in a region of a shrink seating, in a region of adjacent shrinkage influence zones and in a region of a disc body volume, the disc body having side pieces which taper radially outward from the shrink seating in cross-section, the apparatus comprising: at least one ultrasound test head which is arranged on a handling arm of a handling unit, that has at least three degrees of freedom and is connected to a data acquisition device, wherein the handling arm is long and mechanically mounted; and a geometry identification device which is connected to a control device of the handling unit, wherein the handling arm enables the insertion of the ultrasound test head between neighboring disc bodies and turbine blades which are adjacent to them in the radial direction.

The method for ultrasound testing of a disc body, which is shrunk onto a shaft, in the region of the shrink seating and of the adjacent shrinkage influence zone as well as the disc volume, the disc body having side pieces which taper radially outwards from the shrink seating in cross-section, comprises the following steps:

the contour of the disc body is scanned and its geometry is derived in this way;

test parameters and test positions are determined from the disc body geometry in accordance with a predetermined test technique;

a geometric reflection surface is determined; ultrasound test heads are coupled, using the determined test parameters, to the side pieces in order to cover the determined test paths.

It is not necessary for the ultrasound test to know the geometry of the disc body from the start in order to carry out the method. Disc bodies of unknown geometry can now also be subjected to ultrasound testing, since the geometry of the disc body is scanned first of all. This disc geometry is stored in a reference system, in the form of sets of two or three coordinates. Test parameters and the necessary test positions are determined from the stored geometry depending on the predetermined test technique.

During the examination of the hub inner surface of the disc, discrete test positions are preferably determined in such a manner that the entire hub inner surface is covered in the axial direction from these test positions. Owing to the high level of rotational symmetry of the disc, the hub inner surface is also completely accessible for examination in the circumferential direction, by rotation of the shaft.

A method is preferred in which the disc body is scanned without touching it. To this end, the disc body can be scanned by means of light beams, in particular laser beams.

As a result of the fact that the same manipulation system is used for scanning the disc body and the acquisition of the geometry associated with it as for the handling of the ultrasound test heads, there is no longer any need for additional manipulation aids, such as metal positioning sheets, for example. In addition, the auxiliary measurements by measuring probes during coupling of the test heads are avoided, since all the positioning data are processed electrically and are used for direct control of the manipulator.

It is now also possible to test, for example, discs of a turbine shaft, in particular of a low-pressure steam turbine shaft, without said shaft having to be removed from the casing and having to be mounted in a rotating unit. It is possible to carry out the test of the disc body from the joint in the casing, after removal of one half of the casing.

To this end, a corresponding apparatus for carrying out the method has a correspondingly long and mechanically mounted manipulator arm, by means of which the test heads can be guided into the gap between neighbouring discs and the turbine blades which are adjacent to them in the radial direction.

An apparatus is proposed for ultrasound testing of disc bodies, which are shrunk onto a shaft, in the region of the shrink seating, of the adjacent shrinkage influence zone and of the disc volume, which apparatus has a geometry identification device which is connected to a control device of a handling arm, in particular by means of electrical cables. The handling arm is preferably an arm of a robot, which has at least three degrees of freedom. The geometry identification unit preferably has at least one sensor which is arranged on the handling arm and is electrically coupled to an evaluation device. The sensor scans the geometry of the disc body. The signals generated in this way are processed in the evaluation device, and the disc geometry is determined from them. The evaluation device is preferably an electronic data processing unit (a computer). The evaluation unit is also used for driving the control device of the handling arm. Appropriate test positions can be determined in the evaluation unit, and their coordinates can be transmitted to the control device in the form of electrical signals. The control device converts the electrical signals into control signals which drive, for example, electric motors to which the handling arm is connected, in order to move the handling arm with the test head to the corresponding positions. The data acquisition device can also be used for monitoring the positions, so that an error signal is triggered in the event of any discrepancy, by means of which a correction to the movement of the handling arm is initiated. Required value/actual value monitoring is obtained in this way.

All the necessary test parameters, namely the test head position, the ensonification angles and the squint angles, can also be determined from the geometry of the disc body. The measurement principle in this case corresponds, for example, to that described in EP 0 126 383 B1, samples being taken, in particular, at angles of 0°, 45° and 90°. Two test heads, each of which can be arranged on a side piece of a disc, can also be used for testing using the shear method.

It is particularly favourable and time-saving not to use different test heads for different ensonification angles, but to use a transducer array test head whose ensonification angle is adjustable. The required squint angle is produced by rotating the test head by means of a rotatable manipulator arm. The flexibility and adaptability of the test system is enhanced by this measure.

BRIEF DESCRIPTION OF THE DRAWINGS

Further advantages and features of the method and of the apparatus will be explained with respect to a preferred exemplary embodiment which is illustrated in the drawing, in which.

DETAILED DESCRIPTION OF THE INVENTION

Figure 1:
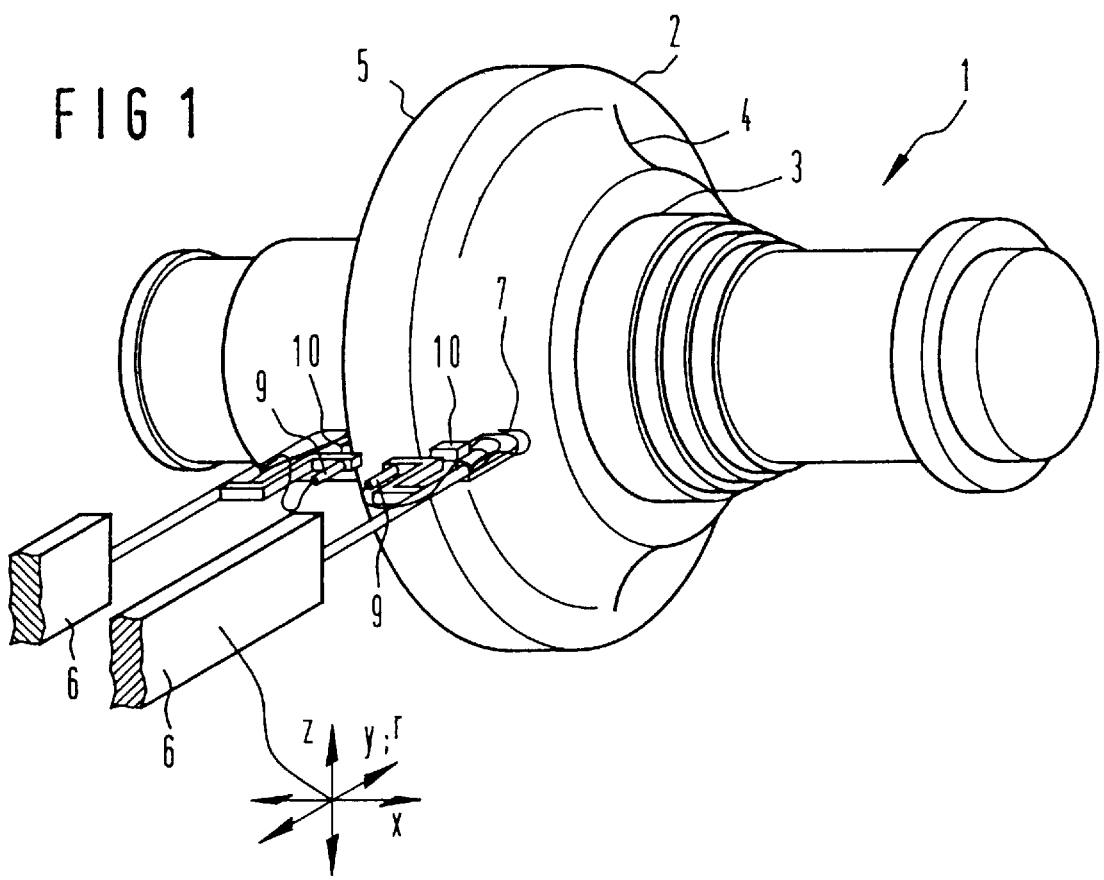
FIG. 1 shows, in perspective, two handling arms with ultrasound test heads and sensors, which are positioned on the side pieces of a disc.

FIG. 1 illustrates, in perspective, a shaft 1 on which a disc body 2 is arranged. The disc body 2 is shrunk onto the shaft 1. The disc body 2 has side pieces 4, 5, which taper radially outwards from the shrink seating 3 in cross-section. Two handling arms 6 are provided to detect the disc body geometry, each of which has at least a sufficient number of degrees of freedom, in particular four, that the ultrasound test heads can be coupled to and manipulated to all those points of the disc surface which are required for the test. Each handling arm 6 can rotate in the direction of the coordinates x, y and z, as well as about its own axis. A sensor 7 is in each case positioned in the front region of each handling arm 6 and scans the disc body 2 in accordance with a predetermined movement sequence of the handling arm 6.

Figure 2:
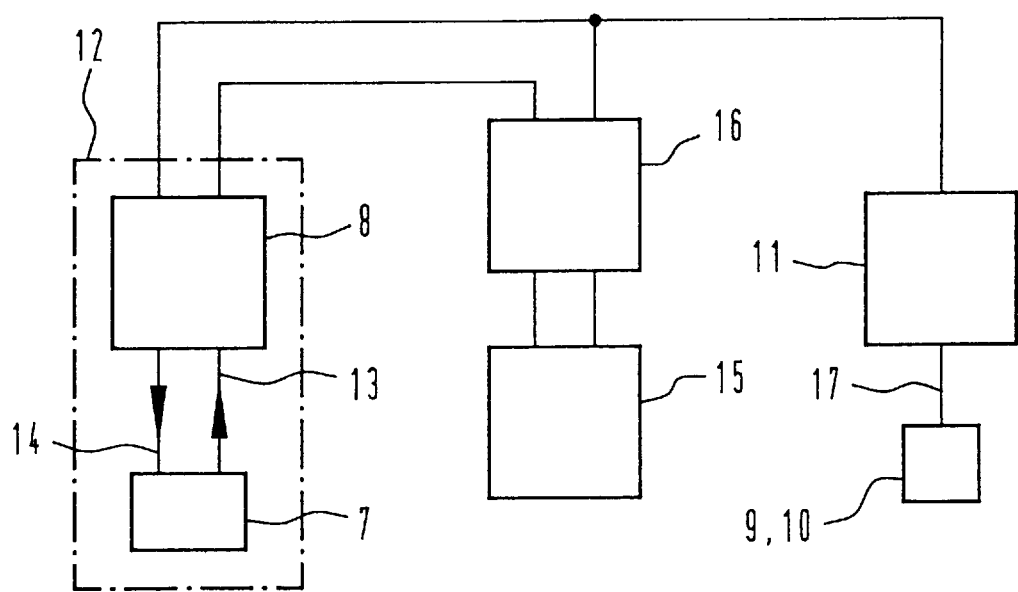
FIG. 2 shows, schematically, the design of an apparatus for ultrasound testing.

The geometry of the disc body 2 is determined in the evaluation device 8 from the scanned points or regions of the disc body 2, according to FIG. 2.

Two ultrasound test heads 9, 10 are arranged in the front region of each handling arm 6 for ultrasound testing of the shrunk-on test body 2. The ultrasound test heads 9, 10, preferably transducer array test heads, are connected to a data acquisition device 11.

The sensor 7, together with the evaluation device 8, forms a geometry identification device 12. The evaluation device 8 is coupled to the sensor 7 by means of electrical cables 13, 14. The geometric data relating to the disc body 2 are transmitted to a control device 16 for the ultrasound test, which control device 16 drives a handling unit 15 having a handling arm 6. The signals which originate from the ultrasound test heads 9/10 are passed on via a cable 17 to the data acquisition device 11. The data acquisition device 11 is also coupled to the evaluation device 8 of the geometry identification device 12. In this way, the associated test path is transmitted directly to the data acquisition device 11, in order to form the determined ultrasound image.

Figure 3:
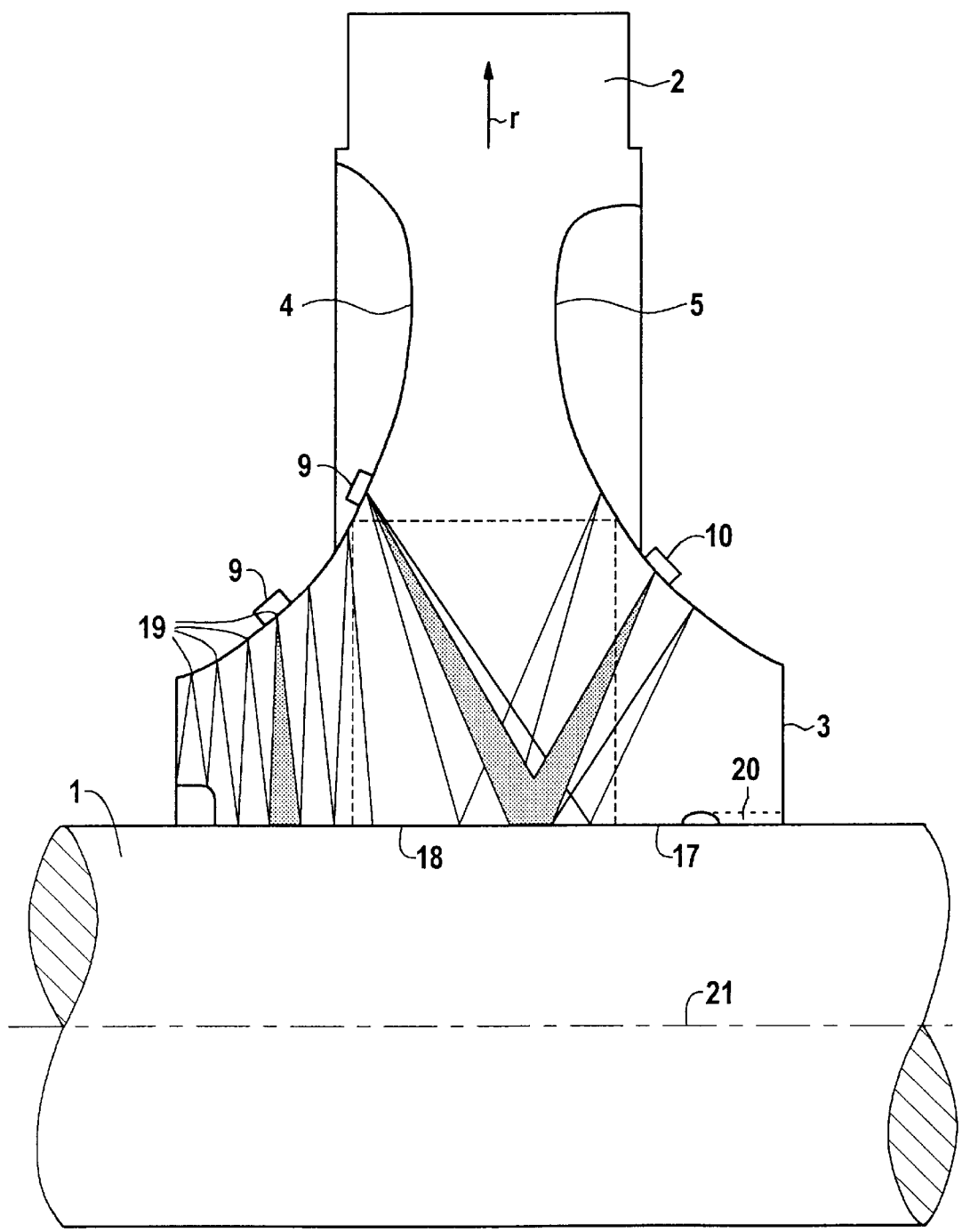
FIG. 3 shows a longitudinal section through a disc.

FIG. 3 shows a longitudinal section through a disc 2, in the direction of the shaft axis 21 of the shaft 1. The disc 2 has side pieces 4, 5 which taper in the radial direction r and run in a concave shape. The disc 2 is located with the axially directed hub inner surface 18 shrunk firmly onto the shaft 1, as a shrink seating. The hub inner surface 18 forms a geometric reflection surface 17, whose position is determined by one or more test heads 9, 10. In order to examine the hub inner surface 18 for cracks, discrete positions 19 are determined for the test heads 9, 10 on the side pieces 4, 5, starting from the contour of the side pieces 4, 5 determined, in particular, via probes which do not make contact. The entire hub inner surface 18 can be covered completely by ultrasound signals, and can thus be examined, in the axial direction, using the position and alignment of the test heads 9, 10. Spatial regions within the volume of the disc 2 can also be examined by means of ultrasound for defects, in particular cracks, likewise in an objective manner, by appropriate positioning of the ultrasound test heads 9, 10. The disc 2 has anti-rotation locks 20. Turbine blades, which are not illustrated, are adjacent in the radial direction, marked by the arrow r. In low-pressure turbine blades, the extent of a gap between adjacent discs 2 and the turbine blades which are arranged on them in the radial direction may be up to more than one metre.

The invention allows the time-saving ultrasound testing of turbine discs, without it being necessary to know their geometry prior to the test. The test can be carried out without removal of the turbine shaft, for example from the joint.

What is claimed is:

1. A method for ultrasound testing of a wheel disc of a turbine rotor shrunk onto a turbine shaft, in a region of a shrink seating and of an adjacent shrinkage influence zone, the wheel disc having side pieces which taper inwardly in a direction radially outward from the region of the shrink seating, the method comprising:

scanning the contour of the wheel disc;
   determining a geometric reflection surface for which occurrences of defects must be taken into account;
   deriving a wheel disc geometry from the results of said scanning the contour and said determining a geometric reflection surface;
   determining test parameter and test positions according to a predetermined test technique for ultrasound test heads, taking into account the wheel disc geometry; and
   coupling ultrasound test heads, using the determined test parameters, to the side pieces and testing along defined test paths.

2. A method according to claim 1, wherein said determining test parameters and test positions comprises determining a number of discrete test positions which ensure that the ultrasound heads carry out a complete examination of a hub inner surface of the wheel disc in a direction parallel to the shaft.

3. A method according to claim 1, wherein said scanning comprises scanning the wheel disc substantially without touching the wheel disc.

4. A method according to claim 3, wherein said scanning comprises scanning the wheel disc by means of light beams.

5. A method according to claim 1, wherein said determining test parameters and test positions comprises determining a test head position as one of the test parameters from geometric data and presets.

6. A method according to claim 1, wherein said determining test parameters and test positions comprises determining an ensonification angle as one of the test parameters from geometric data and presets.

7. A method according to claim 1, wherein said determining test parameters and test positions comprises determining a squint angle as one of the test parameters from geometric data and presets.

8. A method according to claim 1, wherein an orientation of at least one test head is a test parameter with respect to an orientation of a crack.

9. A method according to claim 1, further comprising storing the wheel disc geometry in coordinates in a predetermined reference system.

10. A method according to claim 3, wherein said scanning comprises scanning the wheel disc by means of laser beams.

11. A method according to claim 1, which further comprises rotating the turbine shaft with the wheel disc during the scanning steps while holding the ultrasound test heads substantially stationary.

12. A method according to claim 1, wherein the coupling step comprises varying an ultrasound test head testing angle to an angle other than perpendicular to the contour of the side pieces.

13. In an apparatus for ultrasound testing of a wheel disc shrunk onto a turbine shaft installed in a turbine system, in a region of a shrink seating, in a region of adjacent shrinkage influence zones and in a region of a wheel disc volume, the wheel disc having side pieces which taper inwardly in a direction radially outward from the shrink seating in section, the improvement comprising:

at least one ultrasound test head arranged on a handling arm of a handling unit, said handling unit having at least three degrees of freedom and being connected to a data acquisition device, wherein the handling arm is long and mechanically mounted; and
   a geometry identification device connected to a control device of the handling unit, the handling arm enabling an insertion of the ultrasound test head between neighboring wheel discs and turbine blades adjacent to the wheel discs in a radial direction.

14. An apparatus according to claim 13, wherein the geometry identification device (12) has at least one sensor (7) which is arranged on the handling arm and is electrically coupled to an evaluation device (8).

15. An apparatus according to claim 14, wherein the evaluation device (8) comprises an electronic data processing unit.

16. An apparatus according to claim 13, wherein the ultrasound test head is a transducer array test head which can be set to different ensonification angles corresponding to the geometry of the wheel disc.

17. An apparatus according to claim 14, wherein the control device (16) comprises an electronic data processing unit.

* * * * *